(12) United States Patent
Veenstra et al.

(10) Patent No.: US 11,469,550 B2
(45) Date of Patent: Oct. 11, 2022

(54) MEDICAL COUPLING UNIT AND SENSOR-SIDE CONNECTOR

(71) Applicant: KONINKLIJKE PHILIPS N.V., Eindhoven (NL)

(72) Inventors: Hugo Veenstra, Kleine Brogel (BE); Pierre Hermanus Woerlee, Valkenswaard (NL); Frank Verbakel, Helmond (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 410 days.

(21) Appl. No.: 16/301,462

(22) PCT Filed: Jun. 8, 2017

(86) PCT No.: PCT/EP2017/063889
§ 371 (c)(1),
(2) Date: Nov. 14, 2018

(87) PCT Pub. No.: WO2017/220328
PCT Pub. Date: Dec. 28, 2017

(65) Prior Publication Data
US 2019/0131742 A1    May 2, 2019

(30) Foreign Application Priority Data

Jun. 20, 2016 (EP) .................................. 16175241

(51) Int. Cl.
*H01R 13/64* (2006.01)
*A61B 5/1455* (2006.01)
(Continued)

(52) U.S. Cl.
CPC ......... *H01R 13/64* (2013.01); *A61B 5/14552* (2013.01); *A61B 5/282* (2021.01);
(Continued)

(58) Field of Classification Search
CPC ..... H01R 13/64; H01R 13/6883; H01R 24/60
(Continued)

(56) References Cited

U.S. PATENT DOCUMENTS 4,779,027 A * 10/1988 Sikora .................. H02M 3/335
                                                    315/127
5,287,853 A *  2/1994 Vester ................ A61B 5/14551
                                                     356/41
(Continued)

FOREIGN PATENT DOCUMENTS

EP        0553372      8/1993
EP        1574164      9/2005
(Continued)

OTHER PUBLICATIONS

Michael R. Neuman, "Biopotential Amplifiers", Chapter 6, Medical Instrumentation Application and Design, 4th Edition, Feb. 2009.
(Continued)

*Primary Examiner* — Alexander Gilman

(57) ABSTRACT

The present invention relates to a medical coupling unit for electrical signal transmission between the medical coupling unit (1, 1a, 1b) and a medical sensor (2, 2a) coupled to the medical coupling unit. The medical coupling unit comprises a coupling-side connector (10) comprising a plurality of first electrical contacts (11) in or on a first surface (12) and a plurality of second electrical contacts (13) in or on a second surface (14) opposite the first surface, and a connector interface (15) for analyzing electrical signals available at one or more of the plurality of first and second electrical contacts (11, 13) to detect one or more of presence of a medical sensor coupled to the medical coupling unit, the type of medical sensor coupled to the medical coupling unit, and the orientation of a sensor-side connector of a medical
(Continued)

sensor coupled to the medical coupling unit. The present invention relates further to a sensor-side connector (20).

16 Claims, 11 Drawing Sheets

(51) Int. Cl.
| | |
|---|---|
| *H01R 24/60* | (2011.01) |
| *G01D 21/00* | (2006.01) |
| *G01R 31/69* | (2020.01) |
| *A61B 5/282* | (2021.01) |
| *G01R 27/08* | (2006.01) |
| *H01R 13/66* | (2006.01) |
| *H01R 107/00* | (2006.01) |
| *A61B 5/00* | (2006.01) |
| *A61B 5/276* | (2021.01) |

(52) U.S. Cl.
CPC .............. *G01D 21/00* (2013.01); *G01R 27/08* (2013.01); *G01R 31/69* (2020.01); *H01R 13/6683* (2013.01); *H01R 24/60* (2013.01); *A61B 5/276* (2021.01); *A61B 5/7221* (2013.01); *A61B 2560/0276* (2013.01); *A61B 2562/227* (2013.01); *H01R 2107/00* (2013.01); *H01R 2201/12* (2013.01)

(58) Field of Classification Search
USPC .......................................................... 439/620
See application file for complete search history.

(56) References Cited

U.S. PATENT DOCUMENTS

| | | | | |
|---|---|---|---|---|
| 5,331,275 A * | 7/1994 | Ozaki | ..................... | G01Q 20/04 324/750.22 |
| 5,359,657 A * | 10/1994 | Pelegris | ............. | H01R 13/6666 337/32 |
| 5,563,761 A * | 10/1996 | Apa | ................... | H01R 13/6666 361/111 |
| 5,758,644 A * | 6/1998 | Diab | .................... | G01J 3/0275 600/323 |
| 5,931,791 A * | 8/1999 | Saltzstein | ............. | A61B 5/0205 128/904 |
| 6,179,665 B1 * | 1/2001 | Rossman | ............... | H01R 13/72 439/131 |
| 6,250,936 B1 * | 6/2001 | Armistead | ............. | H01R 9/035 333/24 R |
| 7,271,991 B2 * | 9/2007 | Hoopes | ............... | H01R 13/6666 361/119 |
| 7,508,643 B2 * | 3/2009 | Shreiner | ................. | H04L 12/40 361/117 |
| 7,550,973 B2 * | 6/2009 | Greim | .................. | G01R 33/341 324/309 |
| 7,592,719 B2 * | 9/2009 | Hoopes | .................. | H01R 13/60 307/147 |
| 8,374,665 B2 * | 2/2013 | Lamego | ............. | A61B 5/14551 600/322 |
| 8,742,814 B2 * | 6/2014 | Binder | ............... | G09B 19/0023 327/261 |
| 9,614,337 B2 * | 4/2017 | Lisogurski | ............. | H01R 29/00 |
| 9,825,459 B2 * | 11/2017 | Buehman | ................. | H02H 9/04 |
| 10,285,618 B2 * | 5/2019 | Nebuya | ................ | A61B 5/6831 |
| 2003/0135099 A1 * | 7/2003 | Al-Ali | ................ | A61B 5/14552 600/323 |
| 2005/0113704 A1 * | 5/2005 | Lawson | .................... | A61B 5/00 600/513 |
| 2005/0187440 A1 * | 8/2005 | Abdul-Hafiz | ...... | A61B 5/14551 600/310 |
| 2010/0080563 A1 | 4/2010 | Difonzo | | |
| 2010/0249540 A1 * | 9/2010 | Lisogurski | ........... | A61B 5/0002 600/301 |
| 2011/0077473 A1 * | 3/2011 | Lisogurski | ......... | A61B 5/14551 600/301 |
| 2012/0089369 A1 * | 4/2012 | Abuzeni | ................ | H04L 67/12 702/188 |
| 2013/0117470 A1 * | 5/2013 | Terlizzi | ............. | H01R 13/6683 710/3 |
| 2013/0134989 A1 * | 5/2013 | Cloutier | ............. | A61B 5/14551 324/601 |
| 2014/0275873 A1 * | 9/2014 | Fries | ..................... | H05K 1/117 600/323 |

FOREIGN PATENT DOCUMENTS

| | | |
|---|---|---|
| JP | 2006201154 A | 8/2006 |
| JP | 2014081691 A | 5/2014 |
| WO | 2010075115 | 7/2010 |
| WO | 2010117578 | 10/2010 |

OTHER PUBLICATIONS

Bill Laumeister, 'Lightning Bolts, Defibrillators, And Protection Circuitry Save Lives', Electronic Design, Jun. 23, 2014, http://electronicdesign.com/power/lightning-bolts-defibrillators-and-protection-circuitrysave-lives.
Texas Instruments AFE4403 datasheet, http://www.ti.com/product/afe4403#diagrams.
A.K. Gupta, 'Respiration Measurement Based on Impedance Pneumography', Texas Instruments Application Report SBAA181, Feb. 2011.

* cited by examiner

MEDICAL COUPLING UNIT AND SENSOR-SIDE CONNECTOR

CROSS REFERENCE TO RELATED APPLICATIONS

This application is the U.S. National Phase application under 35 U.S.C. § 371 of International Application No. PCT/EP2017/063889, filed Jun. 8, 2017 published as WO 2017/220328 on Dec. 28, 2017, which claims the benefit of European Patent Application Number 16175241.5 filed Jun. 20, 2016. These applications are hereby incorporated by reference herein.

FIELD OF THE INVENTION

The present invention relates to a medical coupling unit for electrical signal transmission between the medical coupling unit and a medical sensor coupled to the medical coupling unit. The present invention relates further to a sensor-side connector for electrical signal transmission between a medical coupling unit and a medical sensor unit connected to the sensor-side connector.

BACKGROUND OF THE INVENTION

Vital signs monitoring equipment are commonly used for healthcare applications. Vital signs that are frequently monitored include the electrocardiogram (ECG), concentration of oxygen in the blood (SpO2), respiration, blood pressure (invasive: IBP, non-invasive: NIBP) and temperature. Depending on the application and care setting, requirements for the measurement differ such as accuracy, power dissipation, features, etc. An example monitor for use in hospitals is the commercially available Philips IntelliVue MP30. The module works with plug-in measurement server units and is intended for in-hospital use, where the patient remains in the bed. A dedicated connector is provided for each different sensor for the different parameters to be monitored.

There are various scenarios where vital signs of the patient need to be monitored for which specific monitors have been developed. For example, the commercially available Philips IntelliVue MX40 offers better mobility to the patient. It has a dedicated connector and cable, which connect to the top side of the monitor.

For the near future it is anticipated that new monitoring platforms will be developed that can be used across the continuum of care. For good patient comfort, such a next-generation module must be wearable, lightweight and small. This introduces challenges to the connections. Hence, there is a need for providing a medical connector design in support of such a new monitoring platform.

US 2014/0275873 A1 discloses patient monitoring systems having a connector configured to couple a medical sensor to a monitor. According to certain embodiments, the connector may include a layered printed circuit board having a first surface comprising a plurality of electrical contacts and a second surface having a plurality of electrical contacts. The electrical contacts of the first surface and the electrical contacts of the second surface may be configured to enable the connector to be reversible and to electrically couple the medical sensor to the monitor when the connector is in a first orientation or in a second orientation with respect to the monitor.

US 2012/0089369 A1 discloses a medical sensor data manager.

US 2011/0077473 A1 discloses systems, methods, and devices for intercommunication between a medical sensor and an electronic patient monitor.

SUMMARY OF THE INVENTION

It is an object of the present invention to provide a generic medical coupling unit for electrical signal transmission between the medical coupling unit and a medical sensor coupled to the medical coupling unit, which can be used with a multi-measurement module or monitor that can address measurements of various vital signs and can be applied in all scenarios across the continuum of care.

It is a further object of the present invention to provide a corresponding sensor-side connector for electrical signal transmission between a medical coupling unit and a medical sensor unit connected to the sensor-side connector.

In a first aspect of the present invention a medical coupling unit is presented comprising:

a coupling-side connector comprising a plurality of first electrical contacts in or on a first surface and a plurality of second electrical contacts in or on a second surface opposite the first surface, a connector interface for analyzing electrical signals available at one or more of the plurality of first and second electrical contacts to detect one or more of presence of a medical sensor coupled to the medical coupling unit, the type of medical sensor coupled to the medical coupling unit, and the orientation of a sensor-side connector of a medical sensor coupled to the medical coupling unit by evaluating the impedance and/or voltage between predetermined electrical contacts.

In a second aspect of the present invention a sensor-side connector is presented comprising a plurality of first electrical contacts in or on a first surface and a plurality of second electrical contacts in or on a second surface opposite the first surface, one or more internal connections for point symmetrically connecting one or more first electrical contacts with the respective second electrical contact and protection circuitry.

The present invention is based on the idea to provide a generic coupling-side connector, as part of the medical coupling unit, with a limited number of (generic) connections so that various medical sensors can be coupled to the medical coupling unit via the same connector. The medical coupling unit may e.g. be a measurement module or a patient monitor. The medical coupling unit thus supports several measurements including ECG (e.g. up to 12-Lead) and SpO2. In contrast to traditional monitors, the different measurements share a single connector. Depending on the measurement to be performed, the corresponding sensors (which may also include transducers) are connected to the medical coupling unit via the connector. Further, a corresponding sensor-side connector is connected for connecting to the medical coupling unit, which is configured to enable the desired detection of presence, orientation and/or type.

An ECG connector as conventionally used in the known IntelliVue monitor has typically 12 contacts (also called pins). An embodiment of the proposed medical coupling unit supports e.g. up to 12-Lead ECG configurations. Conventional IBP connectors have an equal pin configuration as the ECG connector. A conventional SpO2 connector has 8 pins.

The disclosed medical coupling unit preferably addresses the following issues: It supports multiple vital signs measurements, preferably including ECG (e.g. from 1-Lead up to 12-Lead) and SpO2. It is limited in number of pins/ contacts (e.g. to 20 or less) to enable a compact design. It enables the same protection and safety levels as realized by the existing monitors. It is symmetrical and can be reversed without loss of functionality and safety. It supports (e.g. 2-wire and 4-wire) respiration measurements derived from selected ECG electrode signals. It supports the configuration of an X-Lead ECG function from two Y-Lead ECG modules, for example with X=12, Y=5. By means of spare pins, it is forward compatible.

The medical coupling unit includes a connector interface, which enables detection if a medical sensor is connected to the medical coupling unit and detection of the sensor type and orientation of the sensor-side connector of the sensor. Optionally, the configuration of one or more settings and/or functions of the medical coupling unit (and/or of any electronics included therein) may be controlled according to the connected sensor, and functions (such as leads-off detection (for ECG)) may be included in the connector interface.

In should be noted that the expression "in or on a surface" shall be understood broadly. It does not limit the invention to contacts implemented e.g. from metal tracks on a printed circuit board, but shall be understood to include other types of contacts, such as pins, not using a printed circuit board.

According to a preferred embodiment of the medical coupling unit said connector interface is configured to evaluate the impedance between one first electrical contact and one second electrical contact, serving as presence detection contacts, to detect if a medical sensor is coupled to the medical coupling unit and/or to detect the type of medical sensor. In another exemplary embodiment said connector interface is configured to measure the voltage between one first electrical contact and one second electrical contact, serving as presence detection contacts, in response to a test current driven into one of said presence detection contacts. Evaluating the impedance and/or measuring the voltage is easily possible without much additional circuitry within the medical coupling unit and provides a reliable result.

Said presence detection contacts are preferably central electrical contacts among the plurality of first electrical contacts and the plurality of second electrical contacts, respectively.

There are various options for the connector interface to detect presence, type and/or orientation of the connected medical sensor or sensor-side connector, respectively. In one embodiment, said connector interface is configured to detect the number of shorted contacts to detect presence and/or type of a medical sensor coupled to the medical coupling unit and/or to detect orientation of a sensor-side connector of a medical sensor coupled to the medical coupling unit. In another embodiment, said connector interface is configured to evaluate the impedance between one or more pairs of electrical contacts to detect presence and/or type of a medical sensor coupled to the medical coupling unit and/or to detect orientation of a sensor-side connector of a medical sensor coupled to the medical coupling unit.

The medical coupling unit may further comprise a measurement unit for evaluating electrical signals received at one or more of the plurality of first and second electrical contacts, and a measurement control unit for controlling the configuration and/or evaluation of the measurement unit based on the detected type and/or orientation of a medical sensor coupled to the medical coupling unit. For instance, the measurement mode, the evaluation of measured values, etc. may be controlled in this way.

The medical coupling unit may further comprise a sensor control unit for controlling a connected medical sensor via the coupling-side connector and/or a power supply unit for supplying power to a connected medical sensor and/or to a connected sensor-side connector via the coupling-side connector.

Depending e.g. on the desired design or user requirements, the coupling-side connector may be configured as plug for plugging into a sensor-side connector configured as socket or said coupling-side connector may configured as socket for plugging a sensor-side connector configured as plug into it. Hereby, the plug and socket configuration may also be regarded as male and female configuration.

The point symmetrical connection inside the sensor-side connector provides that the sensor-side connector can be connected to the coupling-side connector in different orientations, but some terminals of the sensor-side connector are always connected to the same nodes inside the medical coupling unit irrespective of the orientation of the coupled sensor-side connector. This is particularly relevant for safety and protection reasons.

In a preferred embodiment of the sensor-side connector it further comprises a reference contact, e.g. a shield contact (e.g. coupled to ground). Further, the sensor-side connector comprises protection circuitry. This e.g. provides for protection of the medical coupling unit, e.g. a patient monitor, during defibrillation pulses.

Said protection circuitry may e.g. comprise one or more sidactors coupled between said reference contact and/or protection resistors coupled between one or more input terminals, to which input signals from the sensor unit are coupled, and one or more of said first and second contacts. The protection elements may generally be embedded inside the sensor-side connector or in the medical coupling unit.

In another embodiment one first electrical contact and one second electrical contact are arranged to connect to a shield contact of a cable connecting the sensor unit to the sensor-side connector. This contributes to operational safety and enables detection if a medical sensor is coupled to the medical coupling unit. Said first and second contacts are preferably central electrical contacts among the plurality of first electrical contacts and the plurality of second electrical contacts, respectively. This may allow coupling the sensor-side connector to the coupling-side connector in different orientation. This is (in addition or alternatively) supported by a rotational-symmetric arrangement of the contacts and by short-circuiting such rotational-symmetric contacts.

For further improving the desired detection the sensor-side connector may further comprise one or more of:
a diode coupled between said first and second contacts,
a first impedance measurement resistor between a first contact and a second contact,
a second impedance measurement resistor between a pair of first contacts or a pair of second contacts, and
an electronic memory (e.g. a chip such as an EEPROM which allows for digital recognition of the presence of a connector and/or of the connector type; the chip may store a serial number and/or sensor specific data).

BRIEF DESCRIPTION OF THE DRAWINGS

These and other aspects of the invention will be apparent from and elucidated with reference to the embodiment(s) described hereinafter. In the following drawings FIGS. 1A, 1B, and 1C schematically show a cross-sectional side view, a top view, and a front view respectively of a first embodiment of a medical coupling unit according to the present invention and of a sensor, FIGS. 2A and 2B schematically show a perspective view and a schematic diagram respectively of another embodiment of a medical coupling unit according to the present invention and of a sensor.

DETAILED DESCRIPTION OF THE INVENTION

Figure 1A:
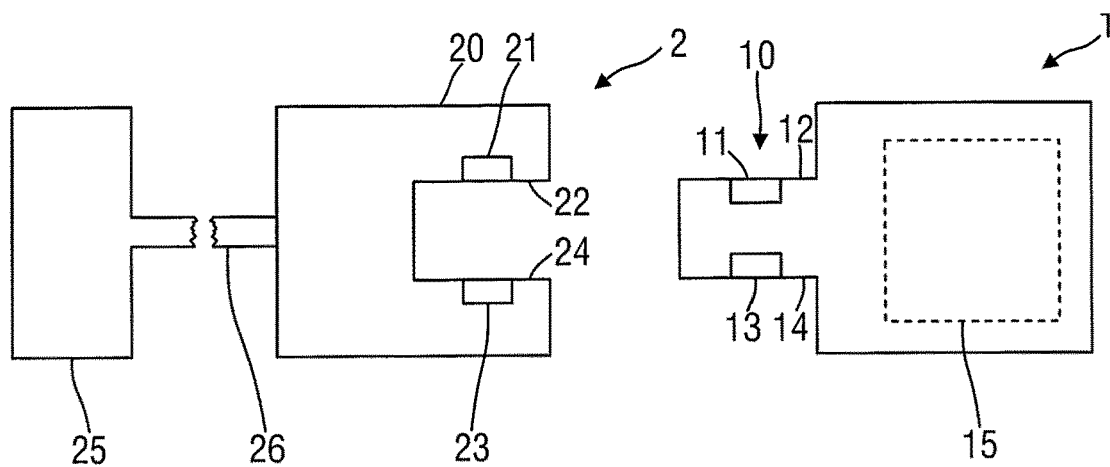
Figure 1B:
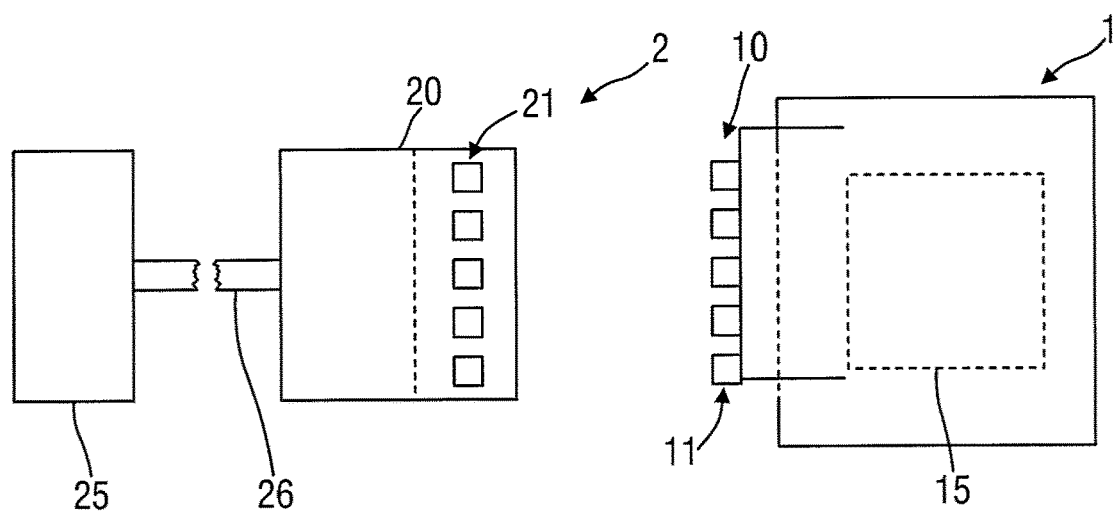
Figure 1C:
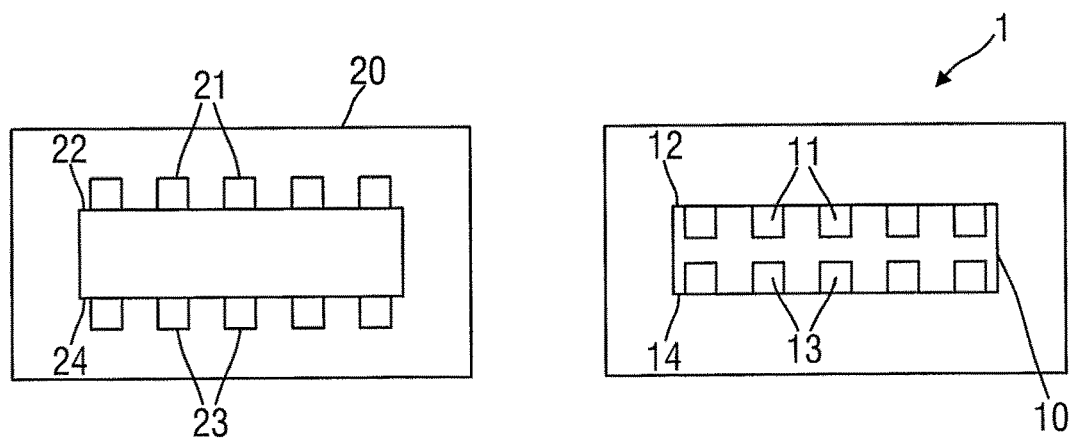

FIGS. 1A, 1B, and 1C show a first embodiment of a medical coupling unit 1 for electrical signal transmission between the medical coupling unit 1 and a medical sensor 2 coupled to the medical coupling unit 1. Various views are shown including a cross-sectional side view (FIG. 1A), a top view (FIG. 1B) and a front view (FIG. 1C).

The medical coupling unit 1 comprises a coupling-side connector 10 comprising a plurality of first electrical contacts 11 in or on a first surface 12 (preferably along a first row) and a plurality of second electrical contacts 13 in or on a second surface 14 (preferably along a second row) opposite the first surface 12. Further, the medical coupling unit 1 comprises a connector interface 15 for analyzing electrical signals available at one or more of the plurality of first and second electrical contacts 11, 13 to detect one or more of presence of a medical sensor 2 coupled to the medical coupling unit 1, the type of medical sensor 2 coupled to the medical coupling unit 1, and the orientation of a sensor-side connector 20 of a medical sensor 2 coupled to the medical coupling unit 1.

The sensor 2 comprises a sensor-side connector 20 comprising a plurality of first electrical contacts 21 in or on a first surface 22 (preferably along a first row) and a plurality of second electrical contacts 23 in or on a second surface 24 (preferably along a second row) opposite the first surface 22. Further, the sensor 2 comprises a sensor unit 25 for sensing a desired measurement parameter and generating electrical signals. The sensor unit 25 is coupled to the sensor-side connector 20 e.g. via a cable 26.

In the embodiment shown in FIGS. 1A, 1B, and 1C the coupling-side connector 10 is configured as plug (i.e. male connector), in which the first electrical contacts 11 are arranged on the top surface 12 of the plug and the second electrical contacts 13 are arranged on the bottom surface 14 of the plug. The sensor-side connector 20 is configured as corresponding socket (i.e. female connector) for insertion of the plug, wherein the first electrical contacts 21 are arranged in or on an upper surface 22 of the socket and the second electrical contacts 23 are arranged in or on a lower surface 24 of the socket. In other embodiments the coupling-side connector may be configured as socket and the sensor-side connector may be configured as corresponding plug. Further, the number of electrical contacts may differ from the number of contacts in the embodiment shown in FIGS. 1A, 1B, and 1C. The sensor 2 may generally be any sensor for sensing a patient's vital sign, such as an ECG sensor, an SpO2 sensor, a blood pressure sensor (IBP—invasive blood pressure; NIBP—non-invasive blood pressure), a temperature sensor, etc.

Thus, the proposed medical coupling unit may support several measurements including ECG (e.g. up to 12-Lead) and SpO2. In contrast to conventional monitors in use today, the different measurements and sensors share a single coupling-side connector. However, only one measurement may be performed at a time. Depending on the measurement to be performed, the corresponding sensors and/or transducers are connected to the medical coupling unit via the coupling-side connector.

The ECG connector as used in the above-cited IntelliVue monitor has 12 pins. The connector supports up to 12-Lead ECG configurations. The two IBP connectors have an equal pin configuration as the ECG connector. The SpO2 connector has 8 pins. Embodiments of the coupling-side connector of the proposed medical coupling unit may addresses one or more of the following issues:

It may support multiple vital signs measurements including ECG (from 1-Lead e.g. up to 12-Lead) and SpO2;

It may be limited in number of pins to 20 or less to enable a compact design;

It may enable at least the same protection and safety levels as realized by the existing monitors;

It may be symmetrical and may be reversed without loss of functionality and safety;

It may support 2-wire and 4-wire respiration measurements derived from selected ECG electrode signals;

It may support the configuration of a X-Lead ECG function from two Y-Lead ECG modules, for example with X=12, Y=5;

By means of optional spare contacts, it may be forward compatible, e.g. used for transmission of digital signals between the medical coupling unit and electronics embedded inside the sensor-side connector or sensor.

Figure 2A:
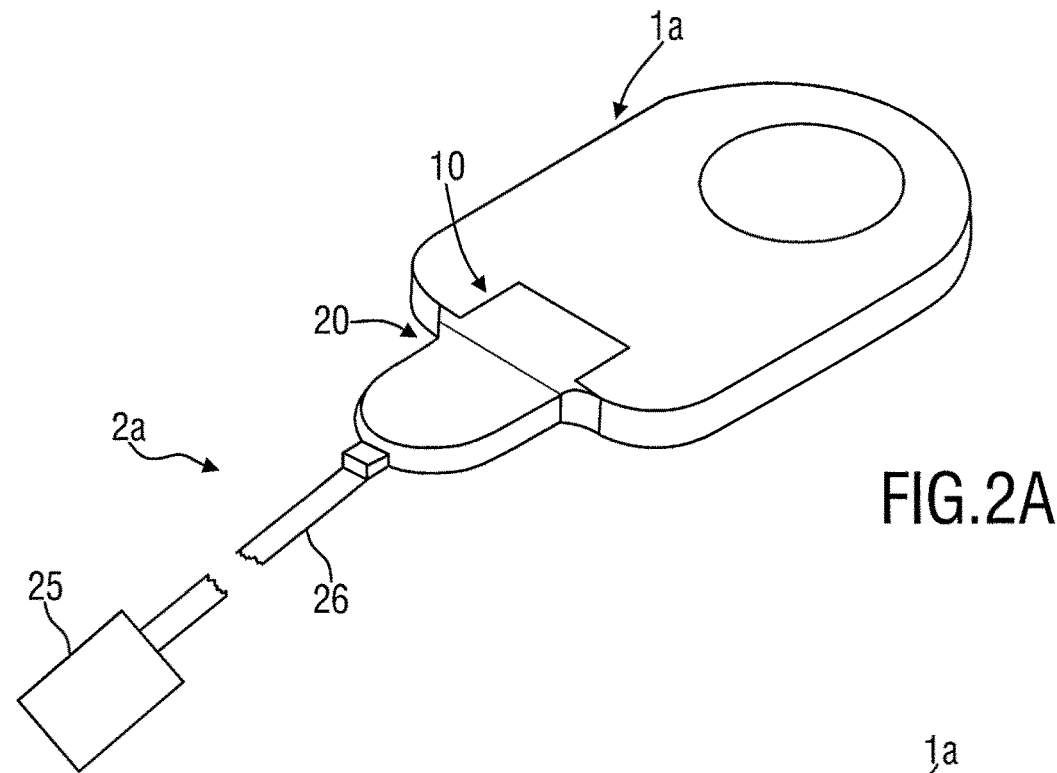
FIG. 2C shows a schematic diagram of still another embodiment of a medical coupling unit according to the present invention, FIG. 3 schematically shows a circuit diagram of a known exemplary input protection scheme for ECG, FIGS. 4A and 4B schematically show 2-wire and 4-wire circuit diagrams respectively of known impedance measurement schemes for ECG, FIG. 5 schematically shows a block diagram of a typical SpO2 front-end, FIG. 6 schematically shows a 16-pin 12-Lead ECG connector, FIG. 7 schematically shows a typical leadwire and trunk cable configuration for ECG, FIG. 8 schematically shows a 10-pin 5-Lead ECG connector, FIG. 9 schematically shows a 14-pin 5-Lead ECG connector enabling 4-wire respiration measurement, FIG. 10 schematically shows an embodiment of a 16-pin fully-symmetrical SpO2 connector, FIG. 11 schematically shows another embodiment of a 16-pin sensor-side connector for SpO2, FIG. 12 schematically shows various signal diagrams of a method for detecting sensor-side connector presence and type based on a detection current, FIG. 13 schematically shows an embodiment of a 10-pin sensor-side connector for SpO2, FIG. 14 schematically shows an embodiment of a 14-pin sensor-side connector for SpO2, and FIG. 15 schematically shows an embodiment of a sensor-side connector supporting active circuitry powered from the medical coupling units via connector contacts.
Figure 2B:
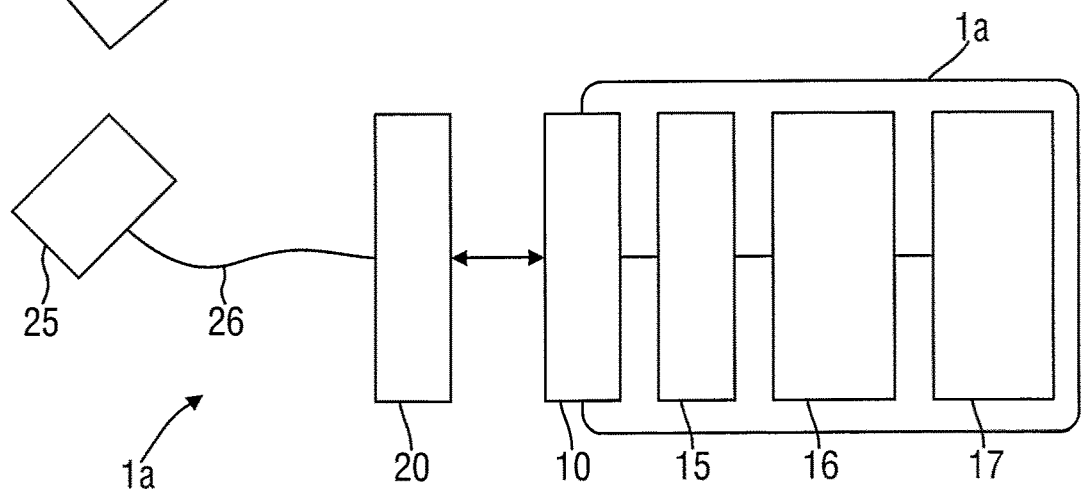
Figure 2C:
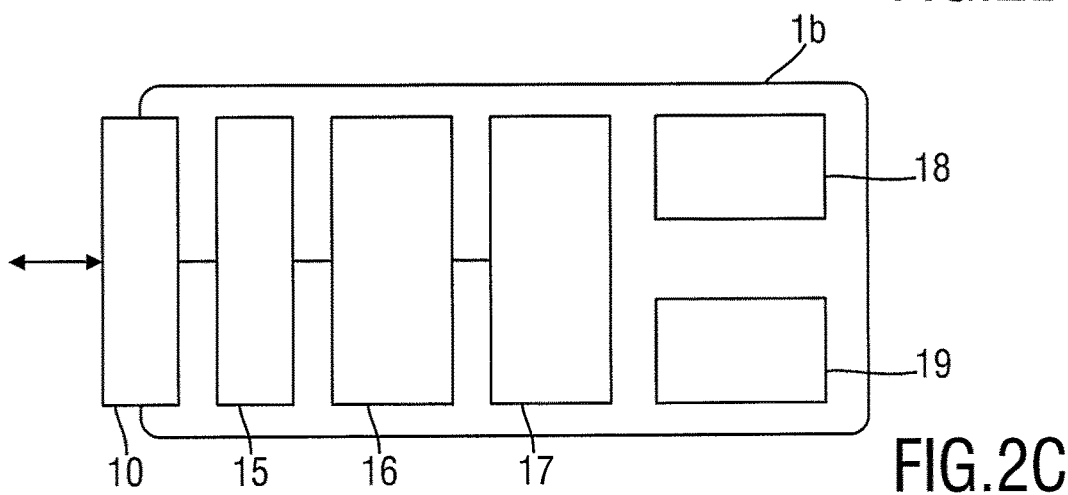

FIGS. 2A and 2B show a perspective view (FIG. 2A) and a schematic diagram (FIG. 2B) of another embodiment of medical coupling unit 1a and a sensor 2a according to the present invention. FIG. 2C shows a schematic diagram of still another embodiment of medical coupling unit 1b.

The medical coupling unit 1a comprises a measurement unit 16 for evaluating electrical signals received at one or more of the plurality of first and second electrical contacts 11, 13, for instance for evaluation the measurements to determine e.g. the heart rate or the oxygen saturation.

Further, a measurement control unit 17 may optionally be provided for controlling the configuration and/or evaluation of the measurement unit 16 based on the detected type and/or orientation of a medical sensor coupled to the medical coupling unit 1a.

The medical coupling unit 1b may additionally comprise a sensor control unit 18 for controlling a connected medical sensor 2 via the coupling-side connector 10.

Further, a power supply unit 19 may be provided for supplying power to a connected medical sensor and/or to a connected sensor-side connector via the coupling-side connector 10.

The connector interface 15, the measurement unit 16, the measurement control unit 17 and/or the sensor control unit 18 may be implemented in hard- and/or software, e.g. a common processor or separate processors.

The primary functions of the medical coupling unit 1a are thus detection if a sensor-side connector is connected to the coupling-side connector, detection (in case of such a connection) of the connector/sensor type and orientation, and control of the configuration of the measurement function according to the coupled sensor. In addition, functions such as leads-off detection (for ECG) may be provided.

For ECG measurements, in the following three embodiments of the coupling-side connector will be described. A first embodiment supports up to 12-Lead ECG with 2-wire respiration measurement. A second embodiment supports up to 5-Lead ECG with 2-wire respiration measurement. A third embodiment supports up to 5-lead ECG with 4-wire respiration measurement.

The 12 leads of a 12-Lead ECG are defined in Table 1. The composition refers to the actual electrodes from which the lead signals are derived. The lead compositions for 1-Lead, 3-Lead, 5-Lead etc. are sub-sets of the 12-Lead ECG. Thus, a connector that supports 12-Lead ECG also supports all (less than 12-lead) ECG measurements.

TABLE 1

| Lead | Composition | Equivalent | Lead type |
|---|---|---|---|
| I | LA − RA | | Bipolar |
| II | LL − RA | | Bipolar |
| III | LL − LA | | Bipolar |
| aVR | RA − 0.5 · (LA + LL) | −(I + II)/2 | Unipolar = augmented |
| aVL | LA − 0.5 · (LL + RA) | (I − III)/2 | Unipolar = augmented |
| aVF | LL − 0.5 · (LA + RA) | (II + III)/2 | Unipolar = augmented |
| V1' | V1 − (LA + RA + LL)/3 | | Unipolar = augmented |
| V2' | V2 − (LA + RA + LL)/3 | | Unipolar = augmented |
| V3' | V3 − (LA + RA + LL)/3 | | Unipolar = augmented |
| V4' | V4 − (LA + RA + LL)/3 | | Unipolar = augmented |
| V5' | V5 − (LA + RA + LL)/3 | | Unipolar = augmented |
| V6' | V6 − (LA + RA + LL)/3 | | Unipolar = augmented |

In addition to the electrodes listed in Table 1, a right-leg electrode RL is often used to provide a reference voltage to the patient. Thus, the sensor-side connector for a 12-Lead ECG measurement must interface to the 10 electrodes LA, RA, LL, V1-V6 and RL.

Figure 3:
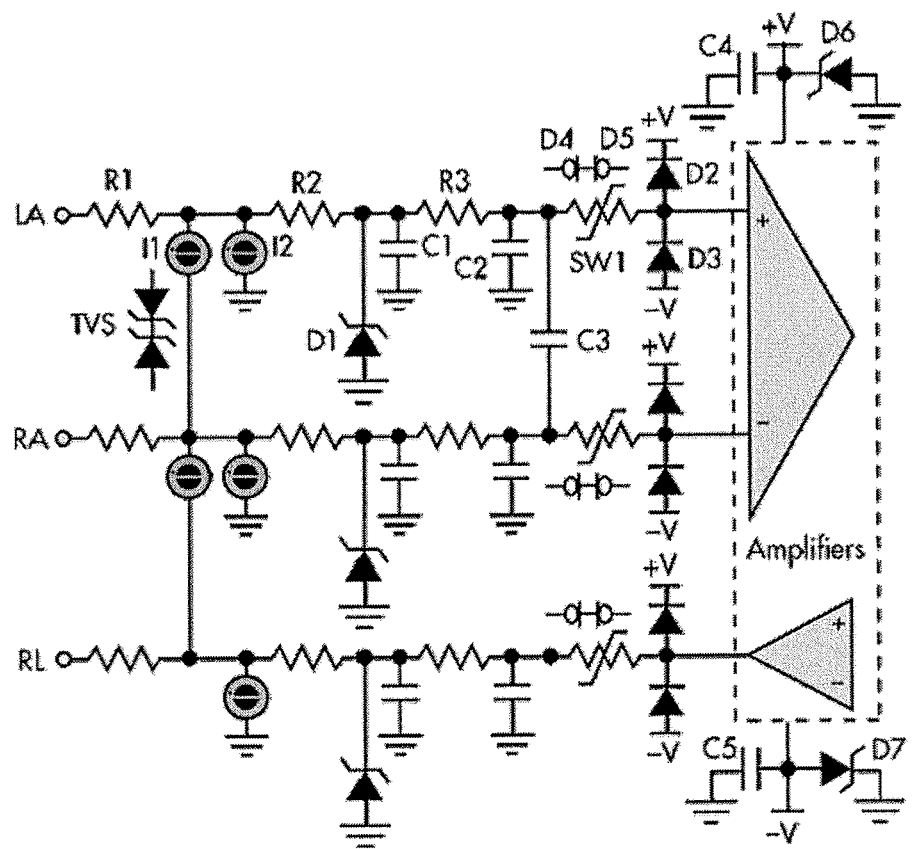

A further aspect relating to the connector is safety and protection. Since embodiments of the proposed medical coupling unit optionally support the full continuum of care, they may be configured to meet the safety and protection requirements even while the patient is undergoing defibrillation treatments. The input network of an ECG front-end usually has multiple protective elements. An example input protection scheme is schematically shown in FIG. 3, which is taken from Bill Laumeister, 'Lightning Bolts, Defibrillators, And Protection Circuitry Save Lives', Electronic Design, Jun. 23, 2014 (currently available at http://electronicdesign.com/power/lightning-bolts-defibrillators-and-protection-circuitry-save-lives).

This example protection scheme addresses a 1-Lead ECG measurement (evaluating Lead I from electrodes RA and LA) and uses electrode RL for right-leg-drive. As seen in FIG. 3, the protection starts with a series resistance that limits the current in the protection device I1 (shown as neon glow lamp) or alternatively TVS (transient voltage suppressor). Moreover, R1 also limits the amount of energy absorbed into the ECG measurement system during patient defibrillation.

Following resistor R1, the protection circuit continues with neon lamp devices I1 and I2. These clamp the maximum voltage to about e.g. 100V (the voltage level depending on the type of neon lamp devices). Device I1 is applied differentially (between electrodes), device I2 is applied single-ended (between an electrode and ground). If the differential protections are removed, an electrode is still protected by device I2. As seen in FIG. 3, the protection for each of the three electrodes used for a 1-Lead ECG is very similar. The approach for input protection can be extended to multi-lead ECG. In a 12-Lead ECG, all 10 electrodes must be protected.

The ECG cable between electrodes and measurement module is often shielded to minimize the impact of interference. The shield is driven from the medical coupling unit side, and must be available on the coupling-side connector. Therefore, the ECG connector for a 12-Lead ECG needs at least 11 connections (for 10 electrodes plus one shield).

A 5-Lead ECG makes use of 5 electrodes, which form a subset of the 10 electrodes used for 12-Lead ECG. If ECG measurements are restricted to 5-Lead ECG, a connector with fewer pins is possible. At least 6 pins are needed (for 5 electrodes plus one shield).

ECG monitor systems often include a respiration detector. Respiration causes small variations in the body impedance, and therefore the respiration frequency can be detected via two or more ECG electrodes based on impedance measurement. An AC-signal is applied to at least two electrodes, and the resulting voltage across these electrodes is measured from which the impedance can be derived. Multiple configurations exist for impedance measurement, and two often used methods are referred to as 2-wire and 4-wire configurations. These configurations are shown in FIGS. 4A and 4B.

The impedance measurement system is shown including protection devices, which are not needed for impedance measurement but are preferred for patient safety in an ECG measurement system.

Figure 4A:
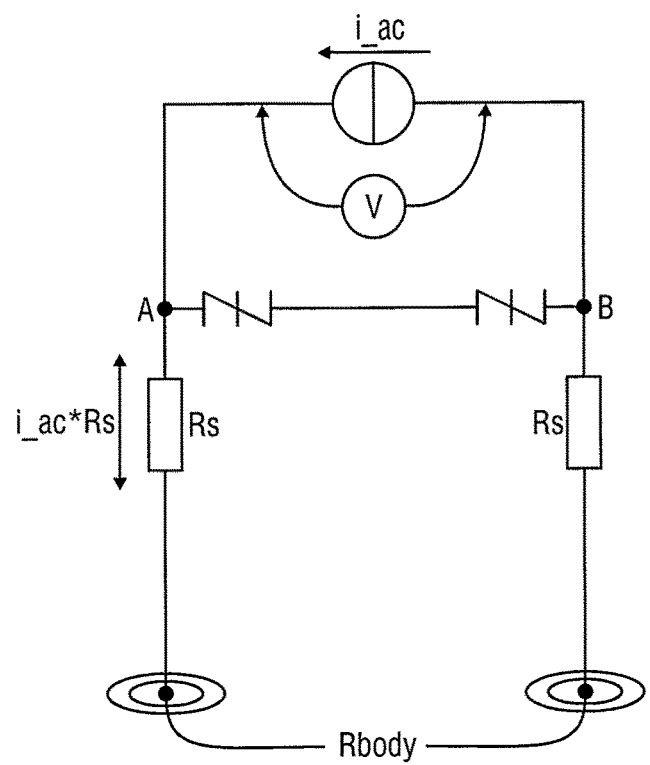
Figure 4B:
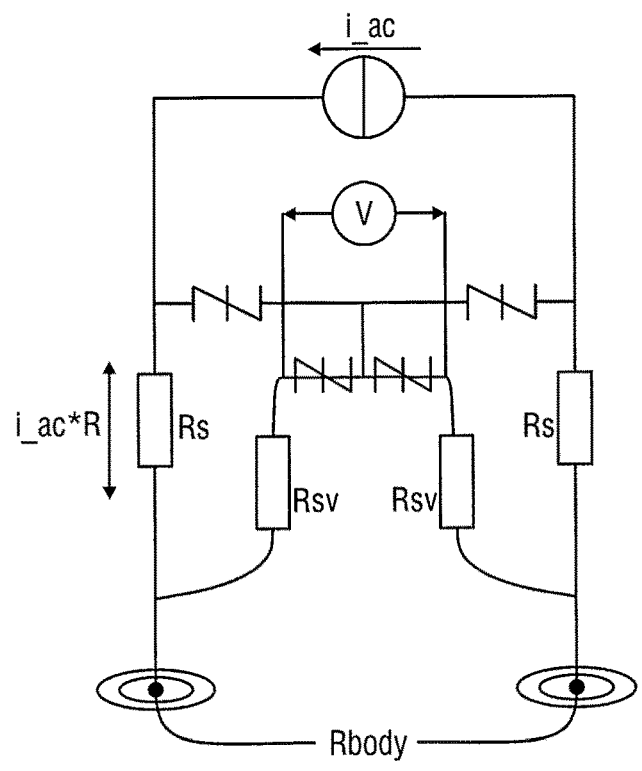

The 2-wire impedance measurement circuitry, shown in FIG. 4A, evaluates the impedance between nodes A and B, which is equal to $RAB = R_{body} + 2R_s$. Resistors $R_s$ represent the protection resistors, shown as R1 in FIG. 3. Obviously, the protection devices (sidactors in FIG. 4A) are also seen in parallel, but these devices typically behave as open circuits for small voltages and therefore do not play a role in the impedance measurement system.

For respiration detection, it is the goal to measure the variation in $R_{body}$ over time. Since this variation is typically small, it is necessary to implement an accurate impedance measurement system. The protection series resistances $R_s$ seen in series with $R_{body}$ reduce the accuracy of the measurement.

In the 4-wire impedance measurement circuitry, shown in FIG. 4B, each electrode has two connections. One connection pair is used to apply the current i_ac; the other pair is used to evaluate the voltage between the electrodes. This improves the accuracy, since the voltage drop across resistors $R_s$ is not seen in the voltage measurement. If it is assumed that the voltage meter has an input impedance $R_{in} \gg R_{sv}$, the voltage drop across $R_{sv}$ is negligible and $R_{sv}$ does not deteriorate the impedance measurement accuracy. The 2-wire respiration measurement does not introduce extra connections to the electrodes and is thus possible for all ECG connectors. As seen in FIG. 4B, the 4-wire measurement method introduces duplicate connections and protection devices to the electrodes, which are used for impedance measurement. These duplicate connections introduce extra pins in the sensor-side connector. In practice, respiration impedance is measured using two out of three electrodes (RA, LA and LL), leading to three extra patient-side connector pins and protection circuits.

Figure 5:
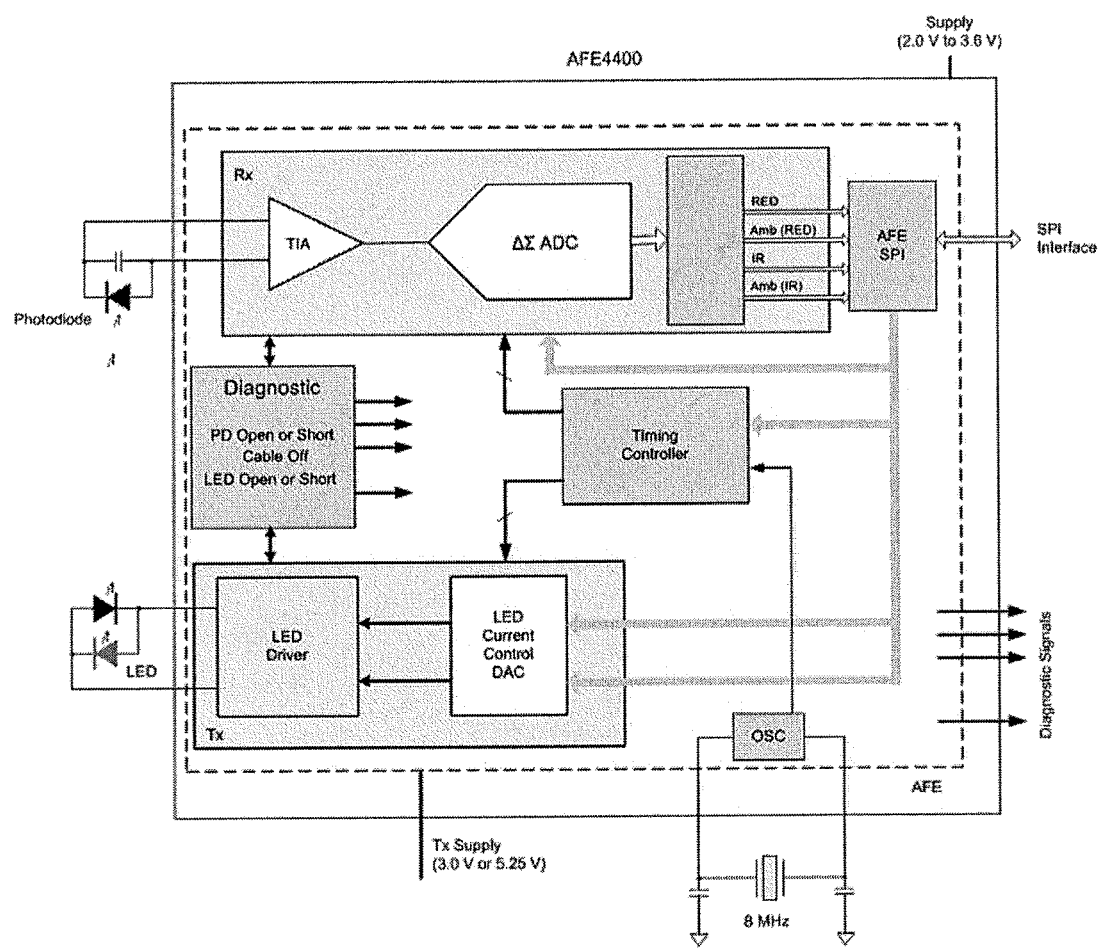

FIG. 5 schematically shows a block diagram of a typical SpO2 front-end, as known from Texas Instruments AFE4403 datasheet (currently available at http://www.ti.com/product/afe4403#diagrams). The measurement method is optical, using two LEDs of different color and one photodiode. The LEDs are usually placed in anti-parallel configuration. The LEDs and photodiode are placed in a probe at a position suited for SpO2 measurements. Usually this is the finger or the ear. The sensor-side connector for SpO2 connects between the front-end and the optical elements (LEDs and photodiodes). As for ECG, to minimize interference, the cable is shielded or double-shielded. The shield is driven from the measurement module side, and must be available on the sensor-side connector.

In some cases, resistors are integrated into the connector to provide information about the transducer to the measurement system. For example, the resistor value inside the connector can be coded in accordance to the LED wavelength. The SpO2 connector needs at least 6 connections (two for the photodiode, two for the antiparallel LEDs, one for a shield and one for a coding resistor). For general purpose and backwards compatibility to some extent (i.e. the sensor can be connected to an existing measurement system using an adapter), two shields and two coding resistors should be supported, leading to at least 8 connections. Since there is no electrical connection between the patient and the SpO2 measurement system, the protection devices as used for ECG are generally not required. The SpO2 measurement system is not electrically disturbed by defibrillation.

In the following, various more detailed embodiments of the proposed medical coupling unit will be described. There are various aspects that will be addressed, including that one connector design should support multiple vital signs measurements, that the connector orientation is reversible without loss of functionality and safety, and that it is possible to integrate (part of) the ECG protection circuitry inside the connector. These aspects are particularly explained for ECG and SpO2 measurements below.

The medical coupling unit, as e.g. disclosed in FIGS. 2A, 2B, and 2C, preferably includes a measurement function. This can be seen as a traditional measurement front-end, performing an ECG or SpO2 measurement. The connector is intended to operate in combination with a connector interface 15 which is able to perform detection if a sensor-side connector is inserted, detection of the sensor-side connector type (e.g. ECG or SpO2), and detection of the orientation of the sensor-side connector. Further, controlling the configuration of the measurement function according to the applied connector may be able, and it may also be possible to move the leads-off detection circuitry that is usually part of the measurement function to the connector interface 15. In the following, example connector electrical designs are discussed together with possible implementations for the connector interface 15.

For ECG measurements, three versions of the sensor-side connector are proposed. A first version supports up to 12-Lead ECG. A second version supports up to 5-Lead ECG. A third version supports up to 5-Lead ECG with 4-wire respiration measurement. The electrodes involved in these configurations are listed in Table 2.

TABLE 2

| ECG configuration | Right Leg Drive electrode | Sense electrodes |
| --- | --- | --- |
| 1-Lead | RL | LA, RA |
| 3-Lead | RL | LA, RA, LL |
| 5-Lead | RL | LA, RA, LL, V1 |
| 12-Lead | RL | LA, RA, LL, V1-V6 |

Independent of the ECG configuration, the connector may preferably interface with the shield of the cable. Besides, each electrode may preferably be protected by a protection circuit. Since the protection devices to protect the ECG measurement electronics during defibrillation pulses are physically large (e.g. the instances I1 shown in FIG. 3) it is and option to integrate these devices into the connector. The series resistors between electrodes and protection devices I1 (e.g. instances R1 in FIG. 3) are then preferably also placed in the cable or the connector. These considerations lead to the 16-pin 12-Lead ECG connector design 30 as a first version for the sensor-side connector outlined in FIG. 6.

Figure 6:
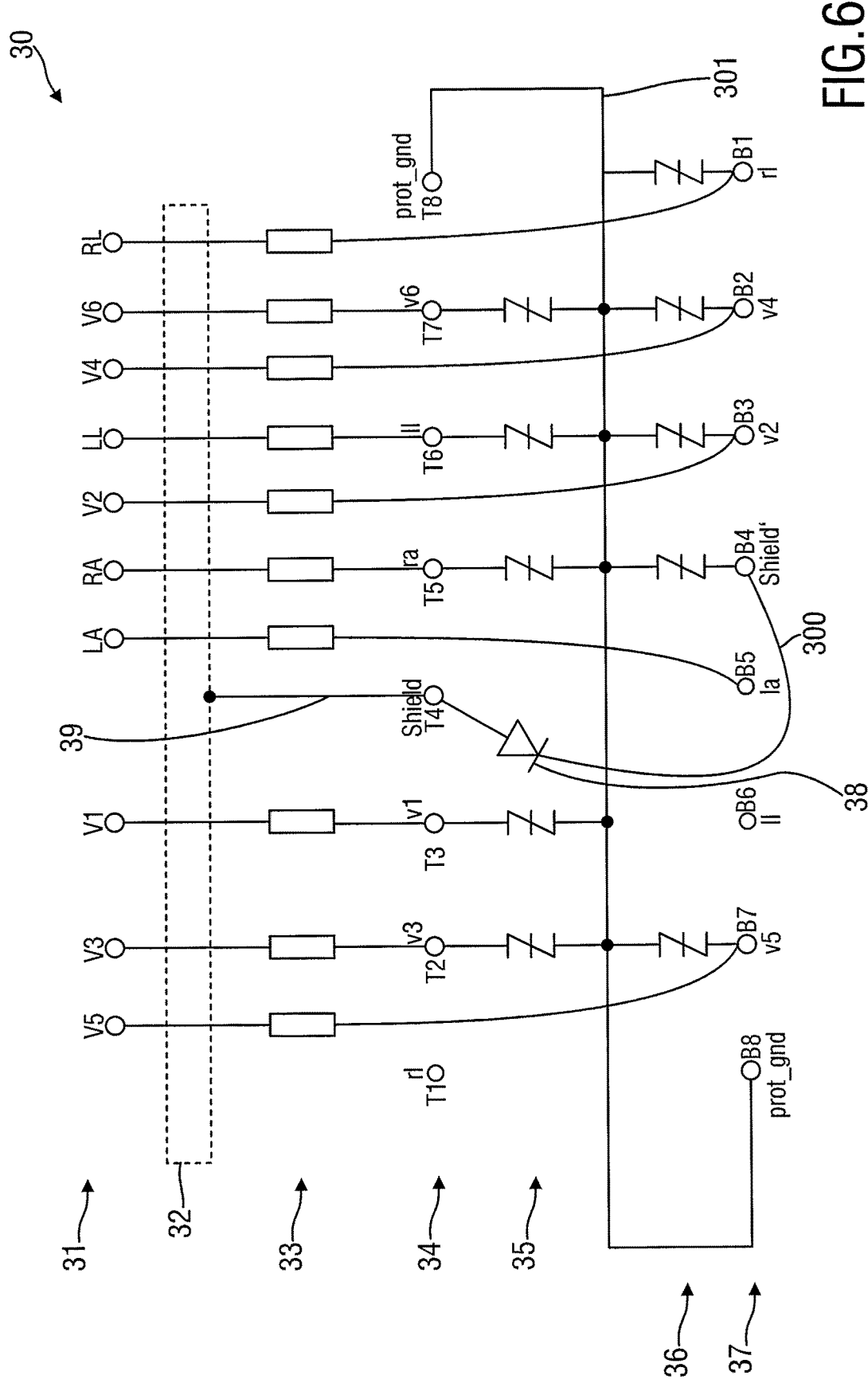

FIG. 6 particularly shows electrode connections 31, a shielded cable 32, protection resistors 33, first contacts 34 (sensor-side connector to coupling unit), sidactors 35, 36, and second contacts 37. Further, a diode 38, a shield connection (or shield contact) 39 and one or more internal connections 300, 301 for point symmetrically connecting one or more first electrical contacts with the respective second electrical contact are provided, wherein the contact 301 serves as reference contact. The resistors 33 and the sidactors 35, 36 generally serve as protection circuitry.

Nodes with identical names are electrically shorted inside the connector 30 (e.g. rl-rl, prot_gnd-prot_gnd and ll-ll). The duplicate prot_gnd connections ensure that the protection reference is always connected between Measurement Module and cable, regardless the connector orientation. The duplicate rl connection ensures that the RL electrode is always connected to the Measurement Module, regardless the connector orientation. The diode between connector pins Shield' and Shield is included to enable sensor-side connector presence detection and function selection by the measurement control unit 17, as will be detailed below. Other pin assignments are also possible. For example, the unipolar lead connections can be interchanged without any impact on functionality, as long as the assignment is known to the connector interface 15.

Considering the connector design depicted in FIG. 6 in a 1-Lead ECG application, the impact of ECG connector orientation shall be described. Signals RA, LA that together form the 1-Lead ECG signal are always applied to the connector interface 15, but depending on the sensor-side connector orientation they may be swapped. It is thus provided that the connector interface 15 detects the connector orientation, as will be described below. A 3-Lead ECG also involves electrode LL. This electrode signal is found on duplicate pins (B6 and T6) and is thus available to the connector interface 15 on the same input, regardless of the sensor-side connector orientation. Extensions to 5-Lead and other configurations, up to 12-Lead, involve additional electrode signals that are available at only a single connector pin. Thus, the sensor-side connector orientation should be known for proper operation.

It should be noted that in FIG. 6 and in subsequent figures notations provided e.g. at electrode connections 31 with capital letters (e.g. "RL") shall indicate a particular signal at a connection on the sensor side, whereas notations provided with small letters (e.g. "rl") shall indicate the same signal as provided at a contact of the sensor-side connector, e.g. in FIG. 6 behind the protection resistor. The proposed sensor-side connector for ECG may include protection networks constructed from resistors and sidactors for all electrode connections. Alternative devices for sidactors, such as neons or trigards, can also be used. The protection devices are generally present, even if not all electrodes are used or connected (e.g. in 1-Lead, 3-Lead or 5-Lead ECG configurations). The connector supports the workflow that is often used today, where the connection between monitor and electrode is divided between trunk cable 41 (from monitor to trunk connector 42) and leadwire 43 (from trunk connector 42 to electrode 44). A number of alternatives exist for the connections between the sensor-side connector 40 and electrodes 44. A typical configuration is shown in FIG. 7.

Figure 7:
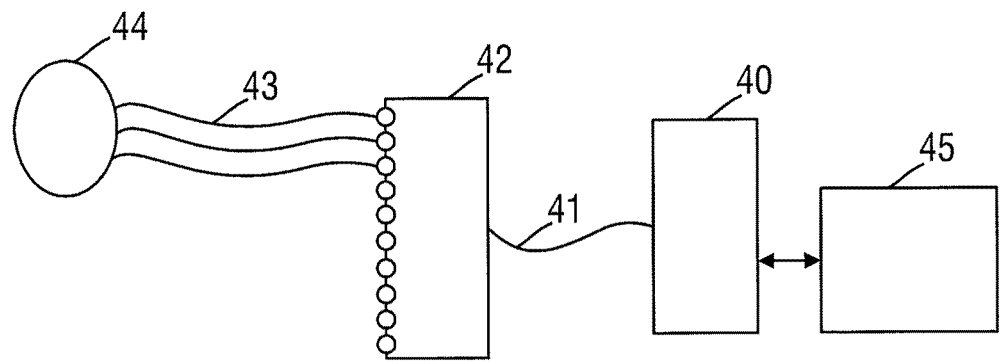

In the configuration shown in FIG. 7 the protection devices can be included in the medical coupling unit 45, in the sensor-side connector 40 or in the connector 42 between trunk cable 41 and leadwire 43.

Figure 8:
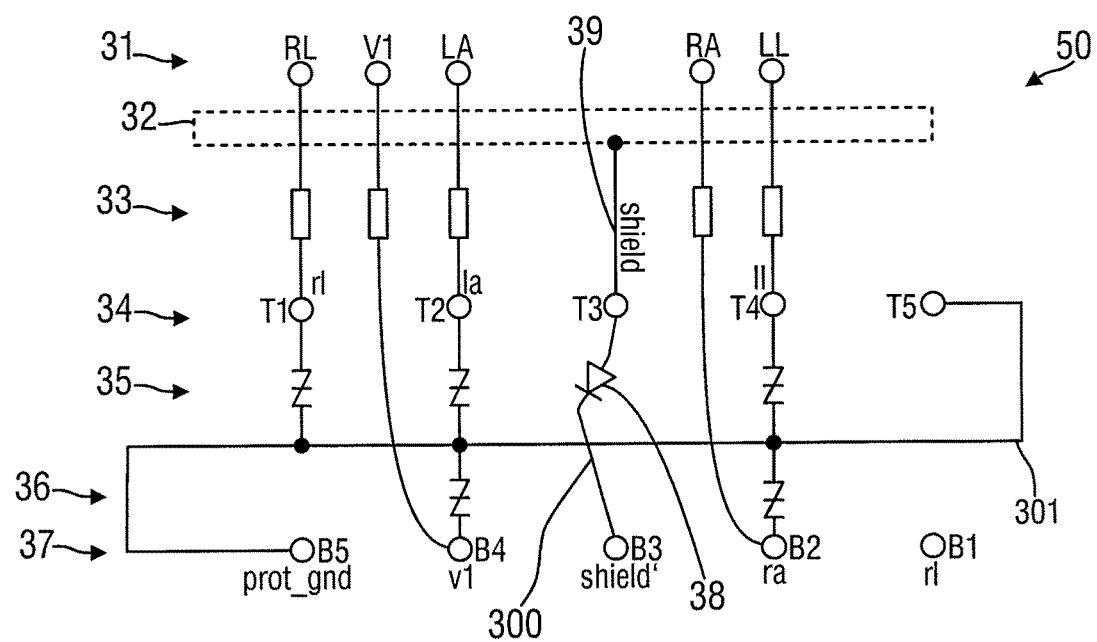

A second version of the sensor-side connector 50, supporting up to 5-Lead ECG, is shown in FIG. 8. The connector 50 is shown with sidactors 35, 36 as protection devices. Also shown are the protection resistors 33, the diode 38 for orientation detection, and the shield connection (or shield contact) 39.

The connector has a duplicate rl connection on pins T1 and B1. This duplication is not strictly necessary, and one of the pins T1, B1 can be used for other purposes. For example, one pin can be redefined from rl to RLD_sum. Connection 'RLD_sum' supports combining two 5-Lead coupling units into a 12-Lead coupling unit. The intention is to achieve an electrical connection between two (or multiple) coupling units via the coupling-side connector. Between two 5-Lead coupling units, electrical connections that can be shared via the coupling-side connectors include prot_gnd, shield and RLD_sum. The RLD_sum pin can be used for the RLD circuitry inside the coupling units, or any other function that requires a shared net between coupling units. Other pin assignments are also possible. For example, the connections LA and RA can be interchanged without any impact on functionality, as long as the assignment is known to the coupling unit.

Figure 9:
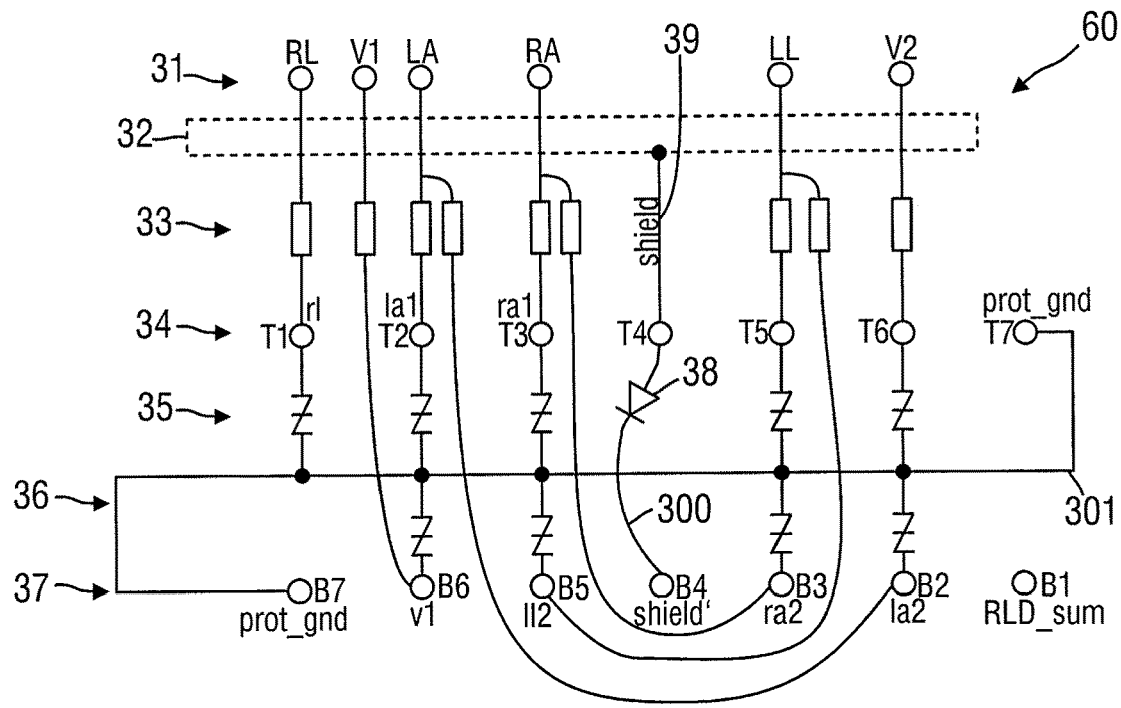

The third version of the sensor-side connector 60, supporting up to 5-Lead ECG with 4-wire respiration, is shown in FIG. 9. This connector 60 supports up to 6 patient electrodes. Such configurations may be used as simplified alternatives to 12-Lead ECG, where the 6 unipolar signals are extrapolated from only two unipolar electrode signals (e.g. connected to V1 and V2). As can be seen, there are duplicate connections for electrodes RA, LA and LL to support the 4-wire impedance measurement method.

The connector interface of the coupling unit can configure which connector pins are used for ECG and respiration measurements, and include appropriate filtering in the respiration and ECG signal paths.

Other pin assignments are also possible. For example, the unipolar lead connections V1 and V2 can be interchanged without any impact on functionality, as long as the assignment is known to the coupling unit.

In the above, three versions of the sensor-side connector for ECG are described, using 16-pins, 10 pins and 14 pins, respectively. In the following SpO2 connector versions for each of the three versions are shown.

Figure 10:
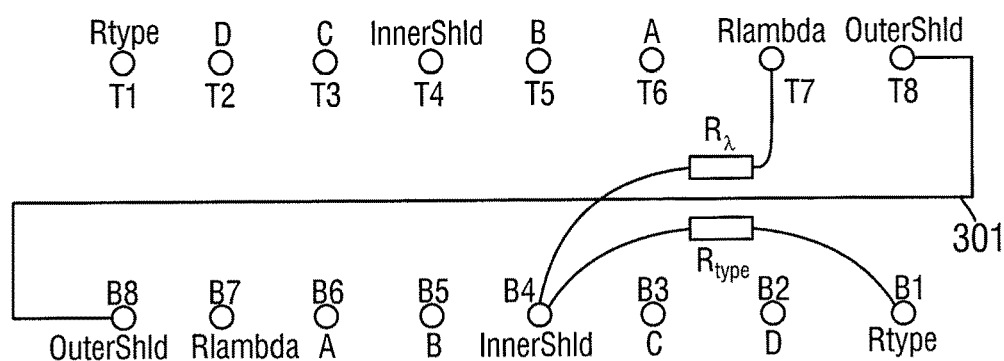

Since there are generally 8 connections required for the SpO2 connector, it is possible to duplicate all connections on a 16-pin connector. With this choice it may not be required to evaluate the sensor-side connector orientation. FIG. 10 shows an embodiment of a 16-pin fully-symmetrical SpO2 connector 70.

Figure 11:
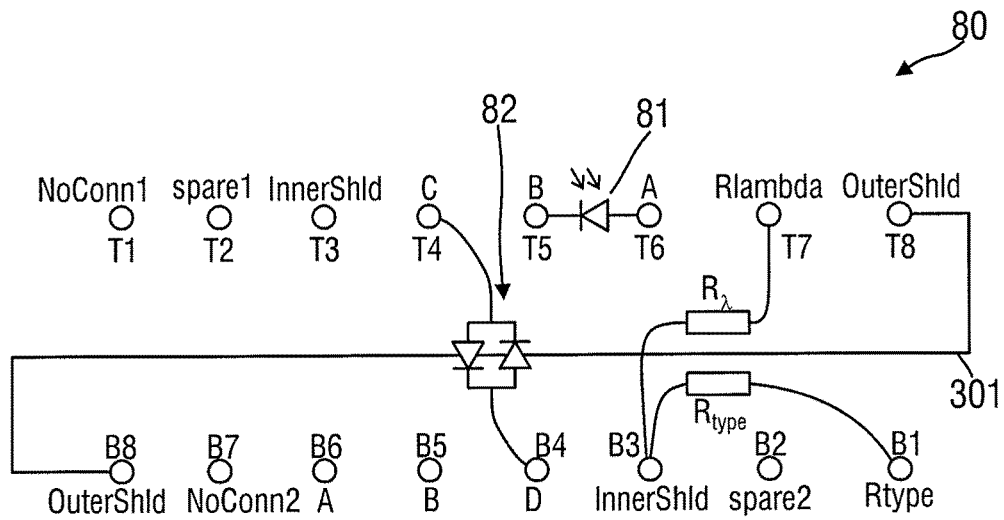

The design shown in FIG. 10 may be further improved since the SpO2 connector 70 provides no spare pins. Such spare pins may be interesting for upwards compatibility, for example to support SpO2 systems operating with additional wavelengths from additional LEDs. This leads to the proposed connector design 80 shown in FIG. 11.

Pins with identical names are shorted inside the connector (e.g., A-A, B-B, InnerShld-InnerShld, OuterShld-OuterShld). Due to the duplicate pins A and B, the photodiode 81 is always properly connected, regardless of the connector orientation. Also, the inner and outer shields are always connected. The two anti-parallel LEDs 82 are also always connected, but their orientation depends on the connector orientation. Since the LEDs 82 differ in wavelength, their orientation should be known to the coupling unit. Pins T4, B4 in FIG. 11 correspond to pins used for signals Shield', Shield for the ECG connector 30 shown in FIG. 6. With this pin assignment, the LED current will not be connected to an ECG electrode in case an ECG sensor-side electrode is accidentally inserted to a SpO2 measurement module. Further, the pins Shield' and Shield of the ECG connector 30 shown in FIG. 6 are used for presence detection and function selection. Presence detection and function selection is thus possible based on the network between pins T4 and B4: a single diode for ECG; two anti-parallel diodes (formed by the SpO2 LEDS) for SpO2; or open circuit (no sensor-side connector applied).

To detect the orientation of the SpO2 connector, resistors Rlambda and/or Rtype can be used. These two resistors are intentionally connected between InnerShld and only a single connector pin. The orientation of the SpO2 connector can thus be evaluated from the impedance between pins B3, T3 (InnerShld) and B1, T1 (Rtype, NoConn1) and/or B7, T7 (Rlambda (also indicated as $R_\lambda$), NoConn2).

The connector interface 15 of the coupling unit 10 is preferably configured to perform the following detection functions:

If a sensor-side connector is connected to the coupling unit;

in case a sensor-side connector is present, the function of the connector (e.g. ECG or SpO2);

the orientation of the sensor-side connector.

Depending on the outputs of the detection, the coupling unit preferably configures itself accordingly. The detection may operate continuously since the sensor-side connector may be disconnected during operation, and a new connector may be inserted at any moment in time.

Figure 12:
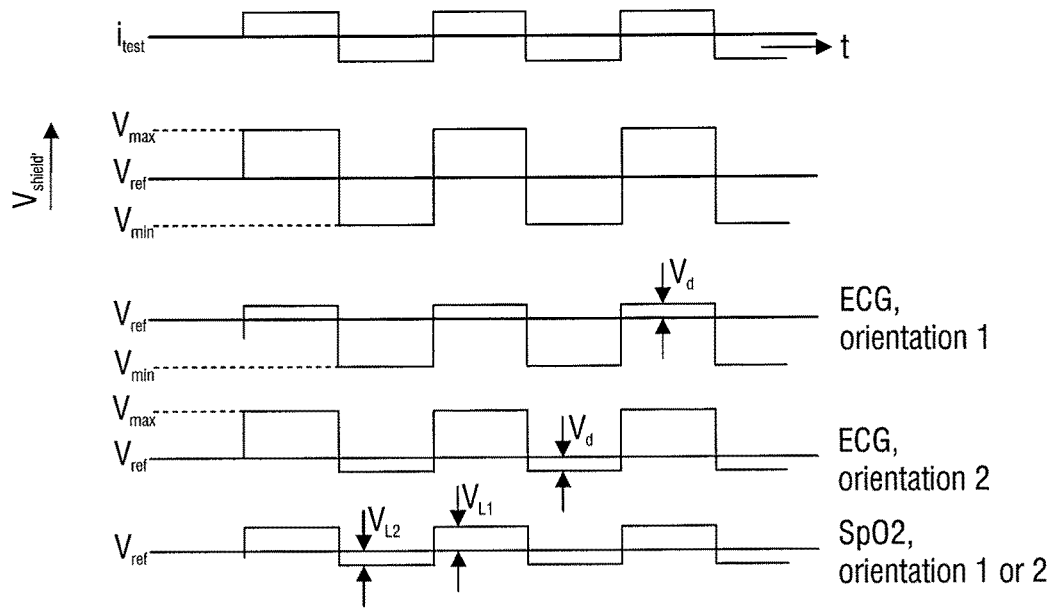

The connector designs shown in FIGS. 6 (for ECG) and 11 (for SpO2) support evaluation of the connector presence and function without driving currents to the patient electrodes. This method is based on the impedance seen between pins T4 and B4 (the corresponding contacts of the coupling-side connector then serving in this example as presence detection contacts). Assuming that pin B4 is kept at a fixed potential Vref (for example, half the supply voltage of the coupling unit) and that a small test current itest is driven from the connector interface into pin T4, the test current can follow a pattern of alternating small positive and small negative currents. The voltage difference between pins T4 and B4 is monitored continuously. Depending on the sensor-side connector configuration, the situations shown in FIG. 12 can occur. FIG. 12 shows various signal diagrams of a method for detecting sensor-side connector presence and type based on a detection current $i_{test}$.

As can be seen, the voltage on pin T4 (Vshield') depends on the applied connector:

If no sensor-side connector is applied, the voltage saturates at levels $V_{max}$ and $V_{min}$ (typically supply and ground levels of the coupling unit).

If an ECG connector is applied, the orientation can be found from the voltage at pin Vshield'. The voltage clamps to a diode voltage $V_d$ (typically 0.8V) for one polarity of the test current.

If an SpO2 connector is applied, the voltage clamps to LED forward voltages VL1 and VL2. It is assumed that $VL1<(V_{max}-V_{ref})$ and $VL2<(V_{max}-V_{ref})$.

Since the SpO2 LED forward voltages are not known, it is not possible to detect the SpO2 sensor-side connector orientation from the detected voltages. However, orientation can be evaluated from the resistors $R_\lambda$, and Rtype, as discussed before.

There are alternative ways to detect the presence, type and orientation of the sensor-side connector applied to the coupling unit. In one embodiment this is based on evaluation of shorted pins inside the sensor-side connector. The number of pins that are shorted inside the connector differs between the proposed ECG and SpO2 sensor-side connectors. For example, pins T3-B3 are not shorted in the 16-pin ECG connector, but the corresponding pins InnerShld-InnerShld inside the 16-pin SpO2 connector are shorted. The connector interface may be based on the evaluations of impedance between pins T3, B3 and T6, B6 (the corresponding contacts of the coupling-side connector then serving in this example as presence detection contacts):

If the impedance between T3 and B3 is high-impedance (open circuit), and the impedance between T6 and B6 is also open circuit, then no sensor-side connector is present.

If the impedance between T3 and B3 is high-impedance (open circuit), and the impedance between T6 and B6 is a short-circuit, then an ECG sensor-side connector is present according to the orientation as shown in FIG. 6.

If the impedance between T3 and B3 is a short-circuit, and the impedance between T6 and B6 is an open circuit, then an ECG sensor-side connector is present according to the orientation opposite to the configuration shown in FIG. 6.

If the impedance between T3 and B3 is a short-circuit, and the impedance between T6 and B6 is also a short-circuit, then an SpO2 connector is present. The orientation can be evaluated from the Rtype and/or $R_\lambda$, pins.

The connector interface 15 (as shown in FIGS. 1 and 2) of the coupling unit may thus perform one or more of these detection methods for detection of configuration and/or orientation. The connector interface 15 may act like a switch matrix, routing connections between the measurement electronics and the coupling unit's input connections. Besides, the connector interface 15 may include detection circuitry for detecting short circuits between connector pins. The short-circuit detection may be based on driving small currents into the connector. Since electrodes may be connected to the patient while the coupling unit is driving a current into one or multiple inputs, part of this current may flow into the patient. The detection currents inside the detection circuitry must thus remain well below safety limits.

Figure 13:
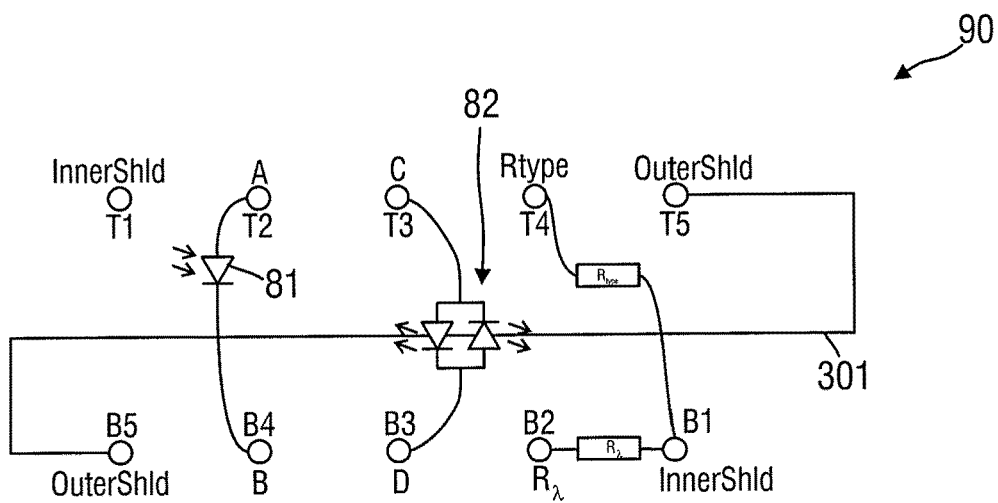

A 10-pin version of a sensor-side connector 90 for SpO2 is shown in FIG. 13. The reduced number of pins makes it no longer possible to duplicate all connections. Connector presence, function and orientation detection operate according to the same mechanisms as for the 16-pin version shown in FIG. 11.

Figure 14:
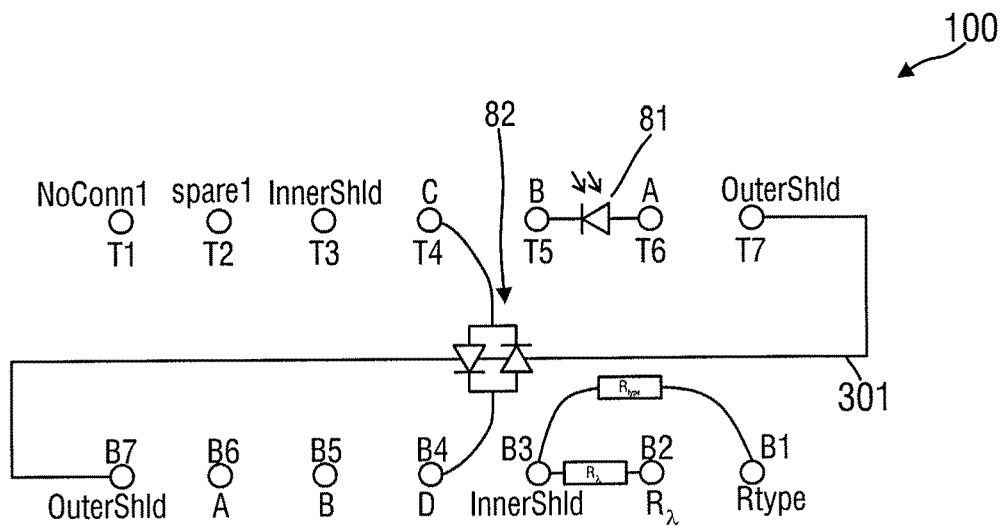

A 14-pin version of a sensor-side connector 100 for SpO2 is shown in FIG. 14. The connections for the photodiode 81 are again duplicated (pins A and B). Connector presence, function and orientation detection operate according to the same mechanisms as for the 16-pin version shown in FIG. 11.

There are further embodiments of the architecture of the medical coupling unit. The medical coupling unit may in one embodiment support multi-measurement and may configure itself based on the sensor-side connector; in this embodiment a single measurement unit 16 may be provided that can be applied for any vital signs measurement. In another embodiment the medical coupling unit may be specific for a single type of vital signs; thus, multiple types of measurement units 16 may be provided (in a single medical coupling unit or in separate coupling units) and each measurement unit is intended to operate with the corresponding sensor-side connector.

The connector designs disclosed herein can work with both options mentioned above. In all cases, patient safety is generally guaranteed, also when a wrong type of sensor-side connector is applied.

The connector designs described so far can be considered as passive connectors. No power supply is transferred between the coupling unit and the sensor-side connector. This is particularly used if existing measurement hardware is reused. It is also possible to design an active connector, shifting part of the measurement hardware to the connector. This solution requires the transfer of power supply and ground to the sensor-side connector. The connector design for an active connector does not fundamentally change. A connector interface in the coupling unit is also provided in this case to detect the type of sensor-side active connector and preferably configure the measurement unit accordingly. Further, the connector interface provides for support of operation with any orientation of the sensor-side connector. A potential advantage of active connectors is that the hardware inside the coupling unit can be more generic.

Figure 15:
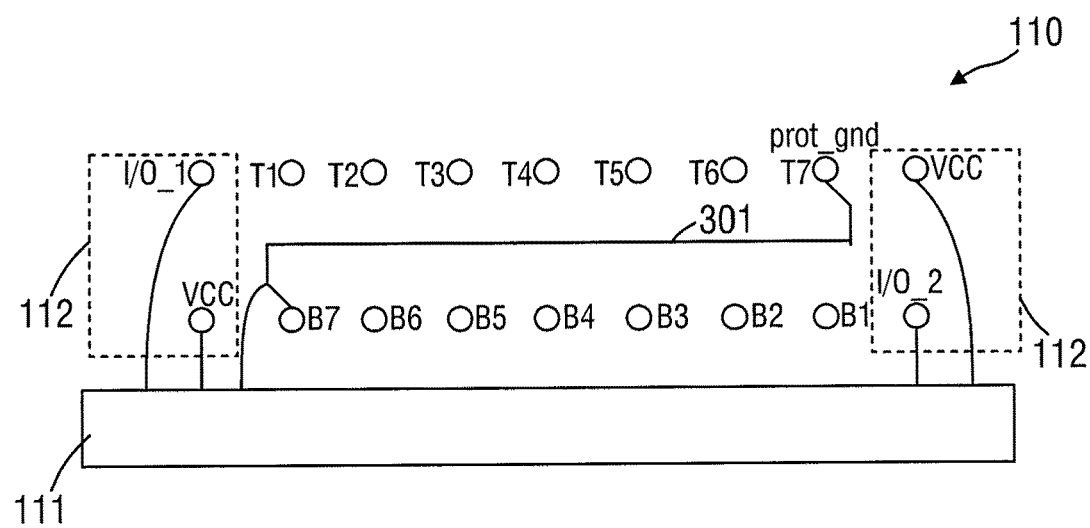

An embodiment of a sensor-side connector 110 that includes active circuitry (analog and/or digital) is shown in FIG. 15. The number of I/O pins can be extended if desired. It includes an active circuit unit 111 and active extension unit(s) 112 to obtain power and other optional signals. Possible functions to include in the connector 110 are:

a digital implementation of the connector orientation detection;

a digital connector ID to identify the connector type or function;

a circuit to perform leads-off detection. Monitoring can include the coupling-side connections and the connections to the coupling unit. A visual indicator (such as an LED) can be included in the connector to provide a simple and quick feedback to the user that the connections are established.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

Any reference signs in the claims should not be construed as limiting the scope.

The invention claimed is:

1. A medical coupling unit comprising:
a coupling-side connector comprising a plurality of first electrical contacts in or on a first surface and a plurality of second electrical contacts in or on a second surface opposite the first surface, wherein a medical sensor is removably coupled to the medical coupling unit by a sensor-side connector that is configured to transmit an electrical signal between the medical coupling unit and the medical sensor, wherein the sensor-side connector comprises a first plurality of sidactors coupled between a reference contact and protection resistors, and a second plurality of sidactors coupled between the reference contact and one or more input terminals, to which input signals are coupled; and
a connector interface configured to analyze electrical signals available at one or more of the plurality of first and second electrical contacts to detect one or more of presence of the medical sensor coupled to the medical coupling unit, and the orientation of the sensor-side connector of the medical sensor coupled to the medical coupling unit by evaluating the impedance and/or voltage between predetermined electrical contacts.

2. The medical coupling unit as claimed in claim 1, wherein said connector interface is configured to evaluate impedance between one first electrical contact and one second electrical contact, serving as presence detection contacts, to detect whether the medical sensor is coupled to the medical coupling unit and/or to detect the type of the medical sensor.

3. The medical coupling unit as claimed in claim 1, wherein said connector interface is configured to measure voltage between one first electrical contact and one second electrical contact, serving as presence detection contacts, in response to a test current driven into one of said presence detection contacts.

4. The medical coupling unit as claimed in claim 2, wherein said presence detection contacts are central electrical contacts among the plurality of first electrical contacts and the plurality of second electrical contacts, respectively.

5. The medical coupling unit as claimed in claim 1, wherein said connector interface is configured to detect a number of shorted contacts to detect presence and/or type of the medical sensor coupled to the medical coupling unit and/or to detect orientation of a sensor-side connector of the medical sensor coupled to the medical coupling unit.

6. The medical coupling unit as claimed in claim 1, wherein said connector interface is configured to evaluate impedance between one or more pairs of electrical contacts to detect presence and/or type of the medical sensor coupled to the medical coupling unit and/or to detect orientation of a sensor-side connector of the medical sensor coupled to the medical coupling unit.

7. The medical coupling unit as claimed in claim 1, further comprising:
a measurement unit configured to evaluate electrical signals received at one or more of the plurality of first and second electrical contacts; and
a measurement control unit configured to control the configuration and/or evaluation of the measurement unit based on the detected type and/or orientation of the medical sensor coupled to the medical coupling unit.

8. The medical coupling unit as claimed in claim 1, further comprising: a sensor control unit configured to control a connected medical sensor via the coupling-side connector and/or a power supply unit for supplying power to the connected medical sensor and/or to a connected sensor-side connector via the coupling-side connector.

9. The medical coupling unit as claimed in claim 1, wherein said coupling-side connector is configured as a plug configured to plug into a sensor-side connector configured as a socket or said coupling-side connector is configured as the socket for plugging the sensor-side connector configured as the plug into it.

10. A sensor-side connector for electrical signal transmission between a medical coupling unit and a medical sensor unit connected to the sensor-side connector and for removably coupling to the medical coupling unit, the sensor-side connector comprising:
a plurality of first electrical contacts in or on a first surface and a plurality of second electrical contacts in or on a second surface opposite the first surface;
one or more internal connections for point symmetrically connecting one or more first electrical contacts with the respective second electrical contact; and
protection circuitry comprising
a first plurality of sidactors coupled between a reference contact and protection resistors, and
a second plurality of sidactors coupled between the reference contact and one or more input terminals, to which input signals from the sensor unit are coupled.

11. The sensor-side connector as claimed in claim 10, wherein one first electrical contact and one second electrical contact are configured to connect to a shield contact of a cable connecting the sensor unit to the sensor-side connector.

12. The sensor-side connector as claimed in claim 11, wherein said first and second contacts are central electrical contacts among the plurality of first electrical contacts and the plurality of second electrical contacts, respectively.

13. The sensor-side connector as claimed in claim 11, further comprising one or more of:
a diode coupled between said first and second contacts (T4, B4);
a first impedance measurement resistor between a first contact and a second contact;
a second impedance measurement resistor (Rte) between a pair of first contacts or a pair of second contacts; and
an electronic memory.

14. A medical coupling unit comprising:
a coupling-side connector comprising a plurality of first electrical contacts in or on a first surface and a plurality of second electrical contacts in or on a second surface opposite the first surface, wherein a medical sensor is removably coupled to the medical coupling unit by a sensor-side connector that is configured to transmit an electrical signal between the medical coupling unit and the medical sensor, wherein the sensor-side connector comprises a first plurality of sidactors coupled between a reference contact and protection resistors, and a second plurality of sidactors coupled between the reference contact and one or more input terminals, to which input signals are coupled; and a connector interface configured to analyze electrical signals available at one or more of the plurality of first and second electrical contacts to detect one or more of presence of the medical sensor coupled to the medical coupling unit, and the orientation of the sensor-side connector of the medical sensor coupled to the medical coupling unit by evaluating the impedance and/or voltage between predetermined electrical contacts;

wherein at least one of the one or more input terminals of the sensor-side connector is configured to engage with a first sensor and at least one of the one or more input terminals of the sensor-side connector is configured to engage with a second sensor, where the first sensor and the second sensor are different.

15. The medical coupling unit of claim 14 wherein, the first sensor and the second sensor are different, and the first sensor and the second sensor are selected from: an electrocardiogram sensor (ECG), a blood-oxygen concentration sensor (SpO2), a respiration sensor, an invasive blood pressure sensor (IBP), a non-invasive blood pressure sensor (NIBP), and a temperature sensor.

16. The medical coupling unit of claim 14, wherein the connector interface is configured to analyze the electrical signals available at the plurality of first and second electrical contacts to detect a sensor type of the first sensor or the second sensor.

* * * * *